United States Patent
Bolmsjö

(12) 
(10) Patent No.: US 6,584,361 B1
(45) Date of Patent: Jun. 24, 2003

(54) METHOD AND DEVICE FOR HEAT TREATMENT OF BODY TISSUE

(75) Inventor: Magnus Bolmsjö, Lund (SE)

(73) Assignee: ProstaLund Operations AB, Lund (SE)

(*) Notice: Subject to any disclaimer, the term of this patent is extended or adjusted under 35 U.S.C. 154(b) by 0 days.

(21) Appl. No.: 09/979,854

(22) PCT Filed: May 8, 2000

(86) PCT No.: PCT/SE00/00905

§ 371 (c)(1),
(2), (4) Date: Nov. 5, 2001

(87) PCT Pub. No.: WO00/67686

PCT Pub. Date: Nov. 16, 2000

(30) Foreign Application Priority Data

May 7, 1999 (SE) .............................................. 9901674

(51) Int. Cl.⁷ .................................................. A61F 7/00
(52) U.S. Cl. ........................ 607/101; 607/102; 607/105; 606/33
(58) Field of Search ..................... 607/96, 99, 101–102, 607/104–105, 156; 606/27–29, 31–33

(56) References Cited

U.S. PATENT DOCUMENTS

| | | |
|---|---|---|
| 4,204,549 A | 5/1980 | Paglione |
| 4,311,154 A | 1/1982 | Sterzer et al. |
| 4,676,258 A | 6/1987 | Inokuchi et al. |
| 4,967,765 A | 11/1990 | Turner et al. |
| 5,084,044 A | 1/1992 | Quint |
| 5,159,925 A | 11/1992 | Neuwirth et al. |
| 5,234,004 A | 8/1993 | Hascoet et al. |
| 5,257,977 A | 11/1993 | Eshel |
| 5,366,490 A | 11/1994 | Edwards et al. |
| 5,421,819 A | 6/1995 | Edwards et al. |
| 5,464,445 A | 11/1995 | Rudie et al. |
| 5,480,417 A | 1/1996 | Hascoet et al. |
| 5,623,940 A | 4/1997 | Daikuzono |
| 5,645,528 A | 7/1997 | Thome |
| 5,861,021 A * | 1/1999 | Thome et al. ............... 607/101 |
| 5,931,860 A * | 8/1999 | Reid et al. ................... 607/101 |
| 5,964,791 A | 10/1999 | Bolmsjö |
| 6,223,085 B1 * | 4/2001 | Dann et al. .................. 607/101 |
| 6,496,737 B2 * | 12/2002 | Rudie et al. ................. 607/101 |

FOREIGN PATENT DOCUMENTS

| | | |
|---|---|---|
| JP | 2121675 | 5/1990 |
| SE | 9502523-5 | 6/1998 |
| WO | WO 9309724 | 5/1993 |
| WO | WO 9401177 | 1/1994 |
| WO | WO 9519142 | 7/1995 |
| WO | WO 9636288 | 11/1996 |
| WO | WO 9702794 | 1/1997 |
| WO | WO 9907325 | 2/1999 |
| WO | WO 9917689 | 4/1999 |
| WO | WO 0045758 | 8/2000 |

OTHER PUBLICATIONS

Jozef Mendecki, Ph.D., et al., *Microwave Applicators for Localized Hypertherma Treatment of Cancer of the Prostrate*, Technical Innovations and Notes, Nov. 1980, vol. 6, No. 11, pp. 1583 through 1588.

* cited by examiner

Primary Examiner—Roy D. Gibson
(74) Attorney, Agent, or Firm—John R. Ley

(57) ABSTRACT

A device for heat treatment of prostate, comprising a treatment catheter with a fluid reservoir and heating means which is arranged within the treatment catheter and emits electromagnetic radiation for heating of the surrounding bodily tissue. The fluid reservoir constitutes an integrated part of the catheter for treatment and is positioned in the catheter so that, when inserted in a patient, it extends to cover the area heated by the heating means between the prostatic apex and bladder neck. The fluid reservoir also constitutes a closed chamber which is connectable via a channel passing through the catheter for treatment. A stop for the heat-absorbing means is embodied distal to said heating means and distal to said heat reservoir.

40 Claims, 2 Drawing Sheets

METHOD AND DEVICE FOR HEAT TREATMENT OF BODY TISSUE

TECHNICAL FIELD OF THE INVENTION

The invention concerns a device for heat treatment of bodily tissue.

Heat treatment yields good treatment results with certain types of disease conditions involving unnatural growth of tissue. The tissue is heated to the extent that it dies. Examples of such disease conditions are certain types of cancer and benign prostate hyperplasia, BPH. During treatment certain portions of the tissue are heated so that tissue death ensues, while other portions of tissue must or should be protected. The temperature in the area of treatment should be at least 50° C. Duration of treatment is typically 1 hour but can be shorter. The disease conditions that are primarily indicated are those which occur in tissue surrounding cavities in the body, for example the prostatic gland.

STATE OF THE ART

Different devices can be used in order to induce heating. Devices for heating by means of laser as well as with microwaves and radio frequencies are common. A technique is known through U.S. Pat. No. 5,257,977, according to which a catheter is provided with a reservoir for fluid. The reservoir is flexible and is connected via channels through the catheter with a heating device located outside the body. A fluid is heated in a heating device and circulated through the channels and the reservoir. The rise of temperature in the reservoir brings about heating of the surrounding tissue.

Since the channels pass through tissue that should not be treated, they must be heat insulated. According to U.S. Pat. No. 5,257,977 the heat insulation is brought about by means of a space filled with gas that surrounds the channels. The function of the heat insulation is very important, for which reason great care and considerable expense must be devoted to this part of the treatment catheter.

A more highly developed catheter for treatment is shown and described in WO 97/02794, according to which a heating device is contained inside an expandable reservoir. The heating device is provided with energy from an assembly outside of the body for heating of fluid inside the reservoir. Some of the disadvantages involving undesirable heating of certain tissue are avoided in this manner. The heating device is designed according to WO 97/02794 as a resistance wire or similar and heats the fluid through convection. The heat transferred from the fluid to the surrounding tissue gives locally good results. A disadvantage is that the effect in the tissue at a farther distance from the reservoir is insignificant.

Heat-treating with a treatment catheter that is equipped with a microwave antenna is also known with the mentioned course of disease. Examples of such microwave treatment are known previously through U.S. Pat. Nos. 5,480,417 and 5,234,004. Characteristic for previously known microwave treatment is that the prostate tissue is heated with microwaves. The intention is to heat parts of the prostate gland so that the tissue coagulates, i.e. dies. The element that emits the microwave radiation consists of a coaxial cable With an antenna at its end that is included in a catheter for treatment. Cooling fluid circulates through the catheter. The intention with the cooling is to protect the prostatic urethra, that is to say the part of the urethra that runs through the prostate gland from being affected and damaged by the heat that is generated by the microwaves. Another reason for cooling the catheter is to transport away waste heat in the coaxial cable.

It has long been viewed as important to protect the part of urethra that passes through the prostate—the prostatic urethra—during microwave treatment of benign prostate enlargement. This protection of the prostatic urethra hinders the treatment from being really effective, however, since parts of the obstructing tissue closest to the urethra are not heated but remain unaffected because of the cooling. The clinical result of heat treatment is dependent on the amount of tissue that coagulates. The degree of coagulation depends in turn on temperature in combination with the length of treatment. The temperature in turn depends on the input of energy and the carrying away of heat by the blood flow. If cooling of the prostatic urethra is done for the purpose of protecting it from being destroyed, the loss of heat energy from the area of treatment is increased, which is counter-productive and severely diminishes the effectiveness of the treatment.

There are also designs with completely uncooled treatment catheters (U.S. Pat. No. 4,967,765). In such embodiments the microwave energy must, however, be limited so that the urethra and penis are not heated due to cable losses in the coaxial cable that conducts the microwaves to the antenna. Because of this restriction, completely uncooled catheters are not preferred, since the microwave power that can then be used (max 30 Watt) is so low that one cannot achieve the high tissue temperature that is needed in order for the coagulation of tissue to occur to the desired extent.

THE INVENTION IN SUMMARY

A purpose of the invention is to increase the effectiveness of treatment with a treatment catheter of previously known technology. The higher treatment effectiveness means shorter treatment times. Alternatively, less microwave power can be used, which increases safety for the patient.

The effectiveness of treatment is increased in that a treatment catheter designed for microwave treatment of the prostate contains a fluid reservoir filled with non-circulating fluid that surrounds the microwave antenna between the prostatic apex and the bladder neck and thus prevents the prostatic urethra from being cooled during treatment The fluid reservoir is heated partly by losses in the antenna device itself that are converted to Joule heat and partly by direct absorption of microwave energy in the fluid itself. The absence of cooling of the prostatic urethra means that less microwave energy can be used to achieve the desired intra-prostatic temperature or alternatively that the treatment time can be shortened. Both possibilities are advantageous for the patient in that they increase safety for the patient and diminish the risk of damage caused by the treatment as a result of high total power output.

Further advantages and special features of the invention emerge from the following description, drawings, and dependent patent claims.

BRIEF DESCRIPTION OF THE DRAWINGS

The invention will now be described in more detail with the aid of examples of embodiments with reference to the attached drawings on which.

THE INVENTION

Figure 1:
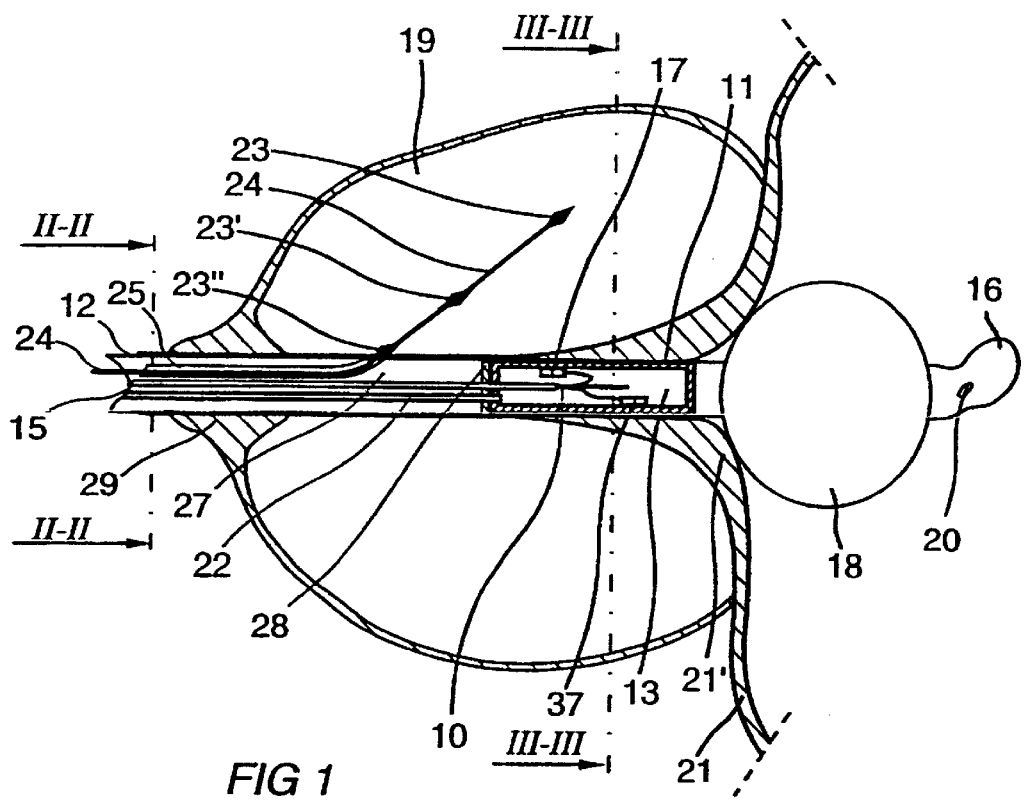
FIG. 1 is a principal cross-sectional view in the longitudinal direction of an embodiment of a treatment catheter according to the invention.

In the embodiment of a treatment catheter 12 according to the invention as shown in FIG. 1 a reservoir 11 isolated from the catheter cooling is positioned in the part of the catheter that is surrounded by the prostate gland. The treatment catheter is in the first place intended for treatment of prostate tissue. Before treatment reservoir 11 is filled via a channel 22 in the treatment catheter 12 with fluid 13, for example sterile water or cooking salt solution. Fluid 13 in the reservoir constitutes a dielectric that improves the adjustment between the microwave antenna and the prostate tissue.

A heating device 10 is provided inside treatment catheter 12 for heating tissue surrounding treatment catheter 12. Heating device 10 emits electromagnetic radiation, preferably in the form of microwaves. Heating device 10 suitably includes a microwave antenna. The energy emitted from heating device 10 is absorbed to a small degree by the fluid in reservoir 11 but the overwhelming part of the energy is radiated out and. absorbed in the surrounding tissue. Energy is supplied via a feed cable 15 from an energy supply unit 14. (See FIG. 4.) In a preferred embodiment first heating device 10 includes an antenna that can be designed, for example, as a monopole antenna, dipole antenna, or a helix antenna. The antenna is covered by a protective sheath 40 up to its radiating section in order to lessen radiation from other sections.

Treatment catheter 12 according to FIG. 1 is introduced through the urethra so that tip 16 extends into urinary bladder 21. A bladder or balloon 18 connected to the treatment catheter is expanded inside urinary bladder 21 and prevents unintended withdrawal of the treatment catheter during the process of treatment. The active part of the treatment catheter is thus centrally located in the tissue that is to be treated, in this case in prostate 19 distal to bladder neck 21'. The treatment catheter 12 is flexible and pliable in order to be introduced flexibly through the urethra to the treatment position.

Figure 2:
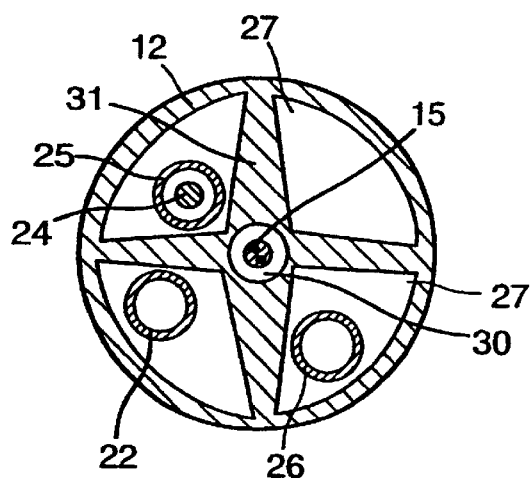
FIG. 2 is a transverse sectional view of the treatment catheter from line II-II in FIG. 1.
Figure 3:
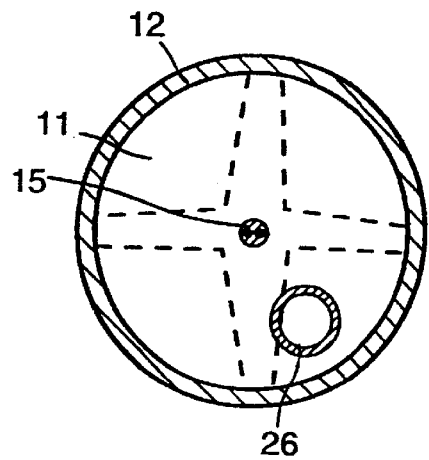
FIG. 3 is a transverse view of the treatment catheter from line III-III in FIG. 1.

In the treatment catheter fluid channel 26 that ends in balloon 18 is also present (see FIG. 2 and 3). Through it fluid can be supplied for expansion of balloon 18 when the treatment catheter is brought into the desired position for treatment. Fluid channel 26 is also used in order to empty balloon 18 after treatment is completed and before the treatment catheter is withdrawn from the urethra. A conventional hypodermic needle or similar is suitably used for the filling and emptying of balloon 18.

Feed cable 15, through which energy is conducted to first heating device 10, is heated as a result of losses. In order to avoid thermally induced damage to tissue outside the area of treatment, for example on sphincter muscle 29 that surrounds the urethra outside of the prostate or to the penis, feed cable 15 is cooled. This is accomplished by providing cooling channels 27 in treatment catheter 12, preferably around feed cable 15. (See also FIG. 2 and FIG. 3.) Cooling channels 27 are embodied according to the invention with a delimiter or stop 28, at which cooling fluid circulating in cooling channels 27 return. In this way cooling of heating device 10 itself and of reservoir 11 is avoided, which in turn means that the energy that needs to be conducted from unit 14 can be diminished. With lower levels of energy, the risk of maltreatment and damage to healthy tissue also diminishes.

Temperature sensors 23, 23', and 23" are arranged on carrier 24 in order to be able to track the temperature development during heat treatment. Carrier 24 can be extended through a channel or tube 25, which runs through the treatment catheter. Carrier 24 or temperature sensor 23 is suitably embodied with, or as, a tip that can penetrate in part a membrane or wall in the treatment catheter and in part the bodily tissue. Tube 25 is embodied so that carrier 24 with temperature sensors 23 is extended out of the treatment catheter at a suitable angle and can be driven out to a suitably radial distance from the treatment catheter.

Heating of tissue thus occurs partly through heating of the fluid contained in reservoir 11 that emits heat directly via heat conduction to adjacent tissue (i.e., the prostatic urethra) and partly through electromagnetic radiation. The total treatment area is thus larger than with conventional heating, where the prostatic urethra is cooled and thus not destroyed during treatment.

Fluid 13 in the reservoir is heated by interaction with microwave antenna 10 to a temperature such that surrounding tissue, i.e., the prostatic urethra, is coagulated. Since the highest temperature is reached in the tissue closest to reservoir 11, the prostatic urethra will to a large degree be affected and therewith be damaged and die. This part of the urethra is, however, regenerated relatively quickly. A special temperature sensor 37 is suitably located in reservoir 11 for continuous measurement of the temperature of fluid 13 in reservoir 11.

A resulting heat profile, i.e. a curve that shows tissue temperature radially outward from the centre of the treatment catheter, is accordingly different from the profile that can be achieved with conventional technology employing a completely cooled catheter or a lack of cooling entirely.

When treatment is finished, the energy supply to heating device 10 is interrupted and reservoir 11 can be emptied of fluid by suction via channel 22. It is not suitable to remove the treatment catheter as long as the reservoir has a temperature such that damage may occur with passage of the reservoir through the body. When catheter 12 is introduced into the urethra with a tip into urine bladder 21, drainage of urine and any other fluid from the urine bladder can occur through a drainage channel provided in catheter 12. The drainage channel runs through the whole catheter 12 and ends with an opening 20 near the tip of catheter 12. With certain types of treatment it can be suitable to leave catheter 12 in place during a certain period of time after the treatment. The function of the drainage channel during this time is also to drain the urine bladder.

As soon as urine passes again through the urethra in the prostate, the treated and dead tissue will be eliminated with the urine. A remaining hollow space in the prostate after the tissue was removed assures the passage of urine in the correct manner. The process of healing including elimination of coagulated tissue can continue for some months.

FIG. 2 schematically shows an embodiment of a treatment catheter 12. Treatment catheter 12 is designed with a number of cavities and channels extending along the treatment catheter. Feed cable 15 runs through a central cavity 30, which is preferably well shielded. Cooling fluid is transported in separated cooling channels 27, preferably in a circulating system. In a first cooling channel 27 a tube 25 for carrier 24 is arranged. In a similar manner fluid channel 26 for balloon 18 and channel 22 for fluid reservoir 11 are arranged in other cooling channels 27. A drainage channel, which ends in opening 20 in the treatment catheter, can be arranged in a similar way in a cooling channel.

The cross section view in FIG. 3 shows an example of how reservoir 11 can be embodied. Essentially the whole internal volume of treatment catheter 12 is occupied by reservoir 11. Partition walls are indicated and can be used, for example, in order to control feed cable 15 and fluid channel 26 for balloon 18. Reservoir 11 can alternatively consist of connected channel elements that constitute a continuation of cooling channels 27 after stop 28.

Figure 4:
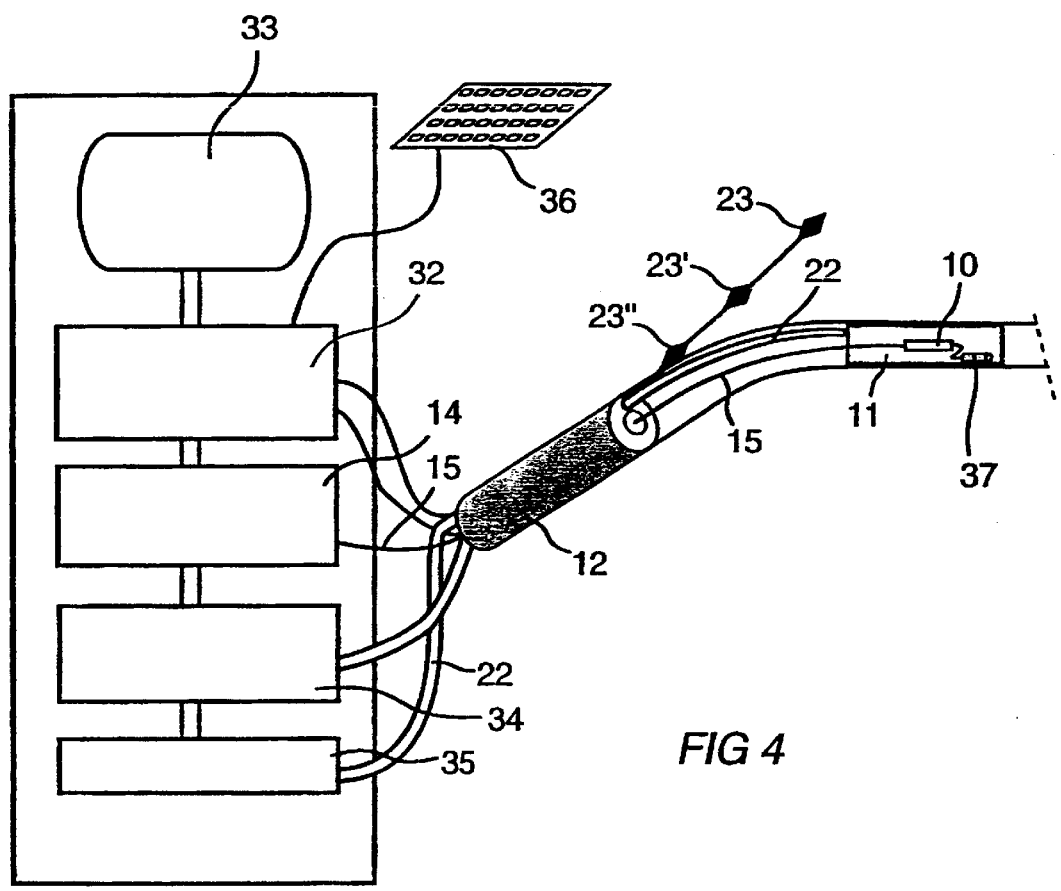
FIG. 4 shows a schematic connection of a treatment catheter to external devices according to one embodiment of the invention.

The block diagram in FIG. 4 schematically shows the various function blocks that can be included in a treatment assembly with a treatment catheter according to the invention. As indicated above, energy is supplied to heating device 10 from energy supply unit 14. A central control unit 32 is operatively connected with energy supply unit 14 and a display unit 33 and with a pumping and cooling device 34 and a fluid supply device 35. Control unit 32 is additionally operatively connected to an input device, for example, in form of a keyboard 36. Control unit 32, keyboard 36, and display unit 33 can also be included in a conventional computer with a monitor and keyboard.

Control unit 32 is operatively connected to temperature sensors 23 and 37 and can control energy supply unit 14 dependent on the current temperature in the area of treatment so that suitable power is supplied to heating device 10. In this manner it is possible to increase the temperature considerably with good safety in fluid reservoir 11 and thus in surrounding tissue so that tissue death occurs in the desired way. Data on temperature from temperature sensors 23 and 37 can also be shown continuously on display unit 33.

Pumping and cooling device 34 is connected to cooling channels 27 and pumps suitable cooling fluid through cooling channels 27 in order primarily to cool feed cable 15 while it is being extended forward to heating device 10. Fluid supply device 35 is used when fluid reservoir 11 is to be filled and emptied. Control unit 32 can monitor the pumping and filling.

A preferred embodiment according to the invention also includes a pressure meter 17 that is operatively connected to reservoir 11 in order to monitor the pressure in the reservoir. Pressure meter 17 is also operatively connected to central control unit 32 so that the pressure in fluid reservoir 11 will affect the process of treatment. The pressure is changed depending on how the treatment proceeds. For reasons of safety the treatment should be interrupted if the pressure in fluid reservoir 11 falls abruptly, for example as a result of the failure of a partition in reservoir 11. In a corresponding way, treatment should be interrupted if the temperature in reservoir 11 becomes so high that the fluid in it boils.

Feed cable 15 can be embodied in the form of a coaxial cable with a protective sheath and an inner conductor. The sheath also constitutes an outer conductor. The inner conductor acts as an antenna beyond the end of the sheath.

What is claimed is:

1. A catheter for insertion into a urethra to perform heat treatment of a prostate which surrounds a prostatic urethra of the urethra in a human being, comprising:
    an antenna located at a position within the catheter adjacent to the prostatic urethra and the prostate upon insertion of the catheter into the urethra to a treatment position at which the treatment is performed, the antenna emitting electromagnetic radiation to heat at least a portion of the prostate surrounding a portion of the prostatic urethra;
    a fluid reservoir within the catheter surrounding the antenna and located to extend along a portion of the prostatic urethra upon positioning the catheter in the treatment position, the fluid reservoir for containing fluid surrounding the antenna to absorb heat from the antenna and from some of the emitted electromagnetic radiation and to apply that absorbed heat through the catheter to the prostatic urethra and prostate tissue surrounding the reservoir;
    a feed cable extending along the catheter from a position at an exterior of the urethra, the feed cable operatively connected to the antenna to conduct energy to the antenna, the feed cable emitting heat as a result of conducting energy to the antenna;
    a cooling channel within the catheter and extending along the feed cable, the cooling channel for conducting cooling fluid to remove the heat emitted from the feed cable and to protect the urethra and the tissue surrounding the feed cable from the heat emitted from the feed cable;
    a delimiter separating the fluid reservoir from the cooling channel; and
    a channel extending through the delimiter for conducting fluid into and out of the fluid reservoir.

2. A catheter as defined in claim 1, wherein:
    the cooling channel and the delimiter permit the cooling fluid to circulate within the cooling channel; and
    the delimiter and the fluid reservoir prevent circulation of the fluid in the fluid reservoir.

3. A catheter as defined in claim 2, wherein:
    the delimiter prevents fluid in the reservoir from circulating with the fluid in the cooling channel.

4. A catheter as defined in claim 1, wherein:
    the delimiter prevents the cooling fluid in circulation within the cooling channel from cooling the fluid in the reservoir.

5. A catheter as defined in claim 1, wherein:
    the delimiter confines the heat in the fluid in the reservoir for application through the catheter to the prostatic urethra and the portion of the prostate, and confines the cooling fluid to remove the heat from the feed cable without transferring sufficient heat from the feed cable to damage the urethra and the tissue surrounding the cooling channel.

6. A catheter as defined in claim 1, wherein:
    the channel extending through the delimiter further extends along the catheter to a position exterior of the urethra.

7. A catheter as defined in claim 1, wherein:
    the reservoir is formed in part by a continuation of the cooling channel extending distally beyond the delimiter.

8. A catheter as defined in claim 1, for use relative to a sphincter muscle which surrounds the urethra at a position proximal of the prostatic urethra, wherein;
    the delimiter is located at a position adjacent to the sphincter muscle upon positioning the catheter in the treatment position.

9. A catheter as defined in claim 1, for use relative to a prostatic apex which surrounds a proximal end of the prostatic urethra, wherein:
    the delimiter is located adjacent to the prostatic apex upon positioning the catheter in the treatment position.

10. A catheter as defined in claim 1, for use relative to a bladder neck which surrounds the urethra where the urethra extends from a bladder of the human being and for use relative to a prostatic apex which surrounds a proximal end of the prostatic urethra, wherein:

the fluid reservoir has a length which extends substantially between the bladder neck and the prostatic apex upon positioning the catheter in the treatment position.

11. A catheter as defined in claim 1, further comprising in combination:

a fluid supply device connected to the channel at a position exterior of the urethra for supplying fluid through the channel to the fluid reservoir.

12. A catheter as defined in claim 1, further comprising:

a heat sensor positioned to sense temperature of fluid within the fluid reservoir.

13. A catheter as defined in claim 12, further comprising in combination:

an energy supply unit connected to the feed cable at a position exterior of the urethra to supply the energy conducted by the feed cable to the antenna; and a central control unit connected to the energy supply unit to control the amount of the energy conducted from the energy supply unit to the feed cable; and wherein:

the heat sensor is operatively connected to the central control unit; and the central control unit controls the amount of energy conducted from the energy supply unit through the feed cable to the antenna in response to the temperature sensed by the heat sensor.

14. A catheter as defined in claim 1, further comprising:

a pressure meter positioned to monitor pressure of fluid within the fluid reservoir.

15. A catheter as defined in claim 14, further comprising in combination:

an energy supply unit connected to the feed cable at a position exterior of the urethra to supply the energy conducted by the feed cable to the antenna; and a central control unit connected to the energy supply unit to control the amount of the energy conducted from the energy supply unit to the feed cable; and wherein:

the pressure meter is operatively connected to the central control unit; and the central control unit controls the amount of energy conducted by the energy supply unit through the feed cable to the antenna in response to the fluid pressure monitored by the pressure meter.

16. A catheter as defined in claim 1, further comprising:

a carrier moveably positioned within the catheter, the carrier having a tip which penetrates into the prostate at a radial distance relative to the catheter upon extension of the carrier when the catheter is positioned in the treatment position; and a temperature sensor connected to the carrier at a position which measure the temperature of the prostate at the radial distance from the catheter.

17. A catheter as defined in claim 16, further comprising in combination:

an energy supply unit connected to the feed cable at a position exterior of the urethra to supply the energy conducted by the feed cable to the antenna; and a central control unit connected to the energy supply unit to control the amount of the energy conducted from the energy supply unit to the feed cable;

a display connected to the central control unit to display information; and wherein:

the temperature sensor is operatively connected to the central control unit; and the central control unit displays information obtained from the temperature sensor relating to the temperature of the prostate at the radial distance.

18. A catheter as defined in claim 17, wherein:

the central control unit controls the amount of energy conducted from the energy supply unit through the feed cable to the antenna in response to the temperature sensed by the temperature sensor.

19. A catheter as defined in claim 16, further comprising:

a plurality of the temperature sensors connected to the carrier at positions which measure the temperature of the prostate at a plurality of different radial distances from the catheter.

20. A catheter as defined in claim 19, further comprising in combination:

an energy supply unit connected to the feed cable at a position exterior of the urethra to supply the energy conducted by the feed cable to the antenna; and a central control unit connected to the energy supply unit to control the amount of the energy conducted from the energy supply unit to the feed cable;

a display connected to the central control unit to display information; and wherein:

the temperature sensors are operatively connected to the central control unit; and the central control unit displays information obtained from the temperature sensors relating to the temperatures of the prostate at the different radial distances.

21. A catheter as defined in claim 20, wherein:

the central control unit controls the amount of energy conducted from the energy supply unit through the feed cable to the antenna in response to the temperatures sensed by the temperature sensors.

22. A method for heat treating a prostate which surrounds a prostatic urethra of a urethra in a human being by using a catheter having an electromagnetic radiation emitting antenna and a feed cable connected to the antenna and extending along the catheter, comprising:

inserting the catheter into the urethra to a treatment position at which the antenna is adjacent to the prostatic urethra and the prostate;

energizing the antenna to emit electromagnetic radiation to heat at least a portion of the prostate surrounding a portion of the prostatic urethra;

surrounding the antenna with fluid in a reservoir to absorb heat from the antenna and from some of the emitted electromagnetic radiation and to apply that absorbed heat through the catheter to a portion of the prostatic urethra and a portion of the prostate surrounding the prostatic urethra;

conducting energy to the antenna through the feed cable;

emitting heat from the feed cable as a result of conducting the energy through the feed cable;

circulating cooling fluid within the catheter along the feed cable to remove heat emitted from the feed cable to protect the urethra and the tissue surrounding the feed cable from the heat emitted by the feed cable; and separating the cooling fluid circulating along the feed cable from the fluid surrounding the antenna.

23. A method as defined in claim 22, further comprising:

confining circulation of the cooling fluid along the feed cable.

24. A method as defined in claim 22, further comprising:

conducting fluid into and out of the reservoir.

25. A method as defined in claim 22, further comprising:

preventing cooling-fluid surrounding the feed cable from circulating in the reservoir.

26. A method as defined in claim 22, further comprising:
preventing fluid in the reservoir from circulating with cooling fluid surrounding the feed cable.

27. A method as defined in claim 22, further comprising:
transferring sufficient heat from the feed cable to the cooling fluid to prevent damage the urethra and the tissue surrounding the cooling channel.

28. A method as defined in claim 22, for use relative to a sphincter muscle which surrounds the urethra at a position proximal of the prostatic urethra, further comprising:
separating the cooling fluid circulating along the feed cable from the fluid surrounding the antenna at a position adjacent to the sphincter muscle.

29. A method as defined in claim 22, for use relative to a prostatic apex which surrounds a proximal end of the prostatic urethra, further comprising:
separating the cooling fluid circulating along the feed cable from the fluid surrounding the antenna at a position adjacent to the prostatic apex.

30. A method as defined in claim 22, for use relative to a bladder neck which surrounds the urethra where the urethra opens from a bladder of the human being and for use relative to a prostatic apex which surrounds a proximal end of the prostate urethra, further comprising:
extending the reservoir substantially between the bladder neck and the prostatic apex.

31. A method as defined in claim 22, further comprising:
sensing a temperature of fluid within the reservoir.

32. A method as defined in claim 31, further comprising:
controlling an amount of the energy conducted through the feed cable relative to the sensed temperature of fluid within the reservoir.

33. A method as defined in claim 22, further comprising:
monitoring a pressure of fluid within the reservoir.

34. A method as defined in claim 33, further comprising:
controlling an amount of energy conducted through the feed cable relative to the pressure to the fluid within the reservoir.

35. A method as defined in claim 22, further comprising:
penetrating a temperature sensor into the prostate from the catheter at a radial distance relative to the catheter; and
measuring the temperature of the prostate at the radial distance from the catheter.

36. A method as defined in claim 35, further comprising:
displaying temperature Information obtained at the temperature sensor.

37. A method as defined in claim 36, further comprising:
controlling an amount of energy conducted through the feed cable in relation to the temperature of the prostate sensed by the temperature sensor.

38. A method as defined in claim 22, further comprising:
penetrating a plurality of the temperature sensors into the prostate from the catheter at a plurality of different radial distances from the catheter.

39. A method as defined in claim 38, further comprising:
displaying temperature information obtained from the plurality of temperature sensors.

40. A method as defined in claim 39, further comprising:
controlling an amount of energy conducted through the feed cable in relation to the temperature of the prostate sensed by the plurality of temperature sensors.

* * * * *